United States Patent [19]

Cullis

[11] 4,303,336
[45] Dec. 1, 1981

[54] METHOD AND APPARATUS FOR MAKING A RAPID MEASUREMENT OF THE HEMATOCRIT OF BLOOD

[75] Inventor: Herbert M. Cullis, Silver Spring, Md.

[73] Assignee: Baxter Travenol Laboratories, Inc., Deerfield, Ill.

[21] Appl. No.: 937,089

[22] Filed: Aug. 28, 1978

[51] Int. Cl.³ .................... G01N 33/48; G01N 21/00; G01N 21/84

[52] U.S. Cl. .................... 356/39; 356/442; 356/432

[58] Field of Search ............... 356/39, 432, 441, 442, 356/41; 250/576; 128/633, 634, 666

[56] References Cited

U.S. PATENT DOCUMENTS

| | | | |
|---|---|---|---|
| 2,700,320 | 1/1955 | Malmros | 356/40 X |
| 3,123,066 | 3/1964 | Brumley | 356/41 |
| 3,830,569 | 8/1974 | Meric | 356/39 |
| 3,923,397 | 12/1975 | Shuck | 356/39 |

OTHER PUBLICATIONS

Skoog et al., Fundamentals of Analytical Chemistry, 1963, pp. 682-683.

Primary Examiner—Vincent P. McGraw
Assistant Examiner—Rodney B. Bovernick
Attorney, Agent, or Firm—Robert A. Benziger; Thomas R. Vigil; Paul C. Flattery

[57] ABSTRACT

The method includes the steps of: placing blood in a transparent tubing; passing intense, coherent light through the tubing and blood; sensing the light passed through the tubing and blood; and, producing a signal related to the amount of transmitted light sensed and indicative of the hematocrit of the blood. The apparatus includes a laser light source for generating the intense, coherent light beam at a wavelength in the red spectrum and an optical photodetector including a silicon diode positioned to receive the transmitted light and an amplifier circuit.

22 Claims, 2 Drawing Figures

METHOD AND APPARATUS FOR MAKING A RAPID MEASUREMENT OF THE HEMATOCRIT OF BLOOD

BACKGROUND OF THE INVENTION

1. Field of the Invention

The field of the invention is a method and apparatus for making a rapid, relatively accurate measurement of the hematocrit of blood.

2. Description of the Prior Art

Heretofore various techniques have been used to measure hematocrit of blood. Hematocrit is the volume of red blood cells in the blood expressed as a percent of volume of red blood cells per 100 milliliters of whole blood. With one technique, a quantity of whole blood is diluted and the red blood cells are counted either by placing a quantity of diluted blood on a slide and counting with a microscope or by using optical counters which measure light scattering of red blood cells as the highly diluted blood is passed through a tubing traversing a light path from a light source to a scattered light detecting photodetector.

In another technique, the blood is centrifuged and the amount of packed red blood cells that have been centrifuged is measured to determine hematocrit.

Although a relatively high degree of accuracy can be obtained using these known techniques for measuring hematocrit, these techniques are very time consuming. Accordingly, it is desirable to provide a rapid means for making a relatively accurate measurement of hematocrit.

The optical density of a blood solution is not linear with the concentration of particles therein. Since hematocrit is a measure of the concentration of particles, specifically red blood cells, in blood, attempts to utilize the optical density or light transmission through a blood sample for measuring concentration of particles have not heretofore been successful. In this respect, optical density and light transmission measurements are used mainly to measure concentration in a solution rather than concentration of discreet particles. Also, discreet particles behave differently in solution since the particles have a tendency to reflect light off the surfaces thereof and often do not permit the light to pass through them.

Also, when the light is reflected, it bounces from one particle surface to another particle surface and such reflected light can make its way through the solution without ever going through a particle. For these reasons, optical density or light transmission measurements are not usually utilized for making measurements of particulate matter in a solution.

In the past however, various methods and apparatus have been proposed for utilizing light in making measurements of various characteristics or blood. Examples of such prior art methods and apparatus for making various analyses of blood, primarily of highly diluted blood, utilizing optical techniques are disclosed in the following U.S. Patents.

| U.S. PATENT NO. | PATENTEE |
|---|---|
| 3,123,066 | Brumley |
| 3,692,410 | Jurany et al. |
| 3,893,767 | Fulwyler et al. |
| 3,905,769 | Carroll et al. |

Moreover, an optical system for measuring hematocrit heretofore has been proposed in U.S. Pat. No. 3,830,569. In this system a laser light is passed through successive samples of blood containing hemolyzed and spherized red blood cells. According to the teachings of this patent, the blood is highly diluted and the light is utilized to enumerate the number of red cells, white cells and platelets in a sample for computing hematocrit. As will be explained in greater detail hereinafter, the method and apparatus of the present invention differ from the method and apparatus disclosed in this patent in that, according to the present invention, a rapid measurement of hematocrit is made by measuring the bulk optical density of blood when an intense, coherent light is passed through the blood. Also, the method and apparatus of the present invention is a non-invasive system which makes measurements exterior of a sterile blood conducting conduit.

Another optical system for measuring hematocrit is disclosed in U.S. Pat. No. 3,923,397. According to the teachings of this patent, hematocrit is measured by passing monochromatic light through a highly diluted blood sample and measuring a characteristic representative of the amount of energy absorbed by the sample. Then, the hematocrit ratio is computed by applying a proportionality factor to the measurements of transmitted light energy by the following expression:

$$H = K(2 - \log_{10} T)$$

where:
H = hematocrit sought to be measured,
T = measured transmitted light energy, and
K = the proportionality factor.

Again, the method and apparatus of the present invention differ from this previously proposed method and apparatus by the measurement of bulk optical density to obtain a rapid, relatively accurate measurement of hematocrit and by the utilization of a linear relationship and proportionality factor derived from a linear curve fit for measurements of the amount of laser light transmitted through, and the hematocrit of the blood through which the laser light is passed, over a given hematocrit range.

SUMMARY OF THE INVENTION

According to the invention there is provided a method for making a non-invasive, non-destructive, rapid, relatively accurate measurement in vivo of the hematocrit of undiluted blood including the steps of: passing the undiluted blood through a liquid confining means having a light transmitting portion, passing intense, coherent, monochromatic light through the light transmitting portion and undiluted blood; sensing the transmittance of light passed through the light transmitting portion and undiluted blood; producing an output signal related to the amount of transmitted light sensed and indicative of the light absorbed by the red blood cells; and multiplying the output signal by a proportionality factor determined from a curve function obtained from an approximated curve fit of absorbance versus hematocrit measurements for measurements of light absorbance by blood having known hematocrits to produce a corrected output signal which is indicative of the hematocrit of the undiluted blood and which can be used to control the flow rate of at least one pump pumping whole blood or a fluid component thereof in a blood processing apparatus.

Further according to the invention there is provided an apparatus for making a non-invasive, non-destructive, rapid, relatively accurate measurement in vivo of the hematocrit of undiluted blood including: liquid confining means having a light transmitting portion and being adapted to receive undiluted blood therein; means for generating an intense, coherent, monochromatic light beam and for directing said light beam through said light transmitting portion of said liquid confining means and the undiluted blood; light sensing means arranged to detect the light that passes through said light transmitting portion and through the undiluted blood from said light generating means to provide an output signal related to the amount of transmitted light sensed and indicative of the light absorbed by the red blood cells; and means for multiplying the output signal generated by the transmitted light sensed by a proportionality factor determined from a curve function obtained from an approximated curve fit of absorbance versus hematocrit measurements for measurements of light absorbance by blood having known hematocrits thereby to produce a corrected output signal which is indicative of the hematocrit of the undiluted blood in said liquid confining means and which can be used to control the flow rate of at least one pump pumping whole blood or a fluid component thereof in a blood processing apparatus.

DESCRIPTION OF THE PREFERRED EMBODIMENT

Figure 1:
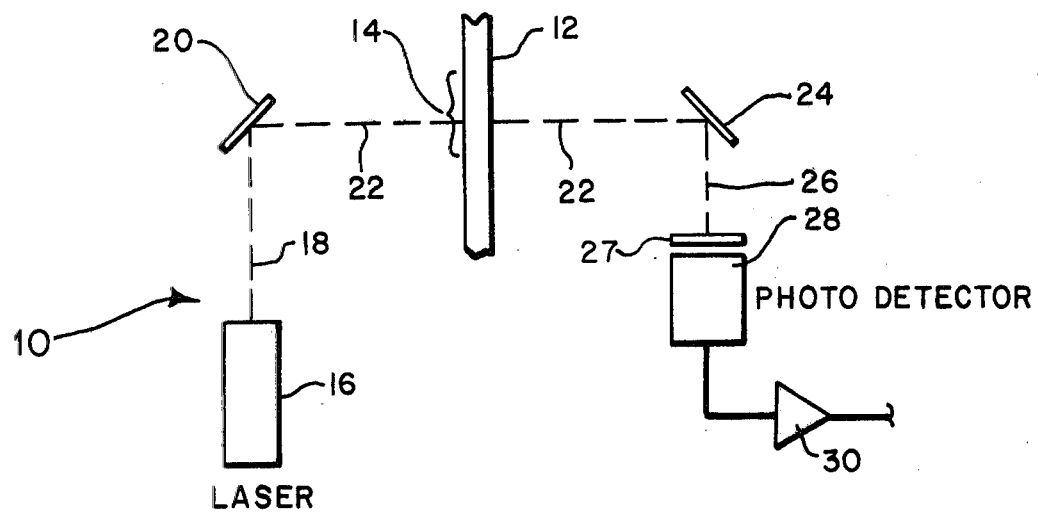
FIG. 1 is a schematic block diagram of the hematocrit measuring apparatus of the present invention.

Referring now to FIG. 1 in greater detail, there is illustrated therein a hematocrit measuring apparatus which is constructed in accordance with the teachings of the present invention and which is generally identified by the reference numeral 10. The apparatus 10 includes fluid confining means defined by a conduit or tubing 12 having a light transmitting portion 14. Preferably the tubing 12 is made of a transparent plastic material. Blood is passed through or placed within the tubing 12.

The apparatus 10 further includes a laser 16 which is adapted to direct a laser light beam along a first path 18 which, in the illustrated embodiment, is generally parallel to the elongate axis of the tubing 12. As shown, the laser light beam is directed along the path 18 to a first mirror 20 which is arranged on one side of the tubing 12 to reflect the laser light beam along a second path 22 which is 90° to the first path 18 and which is normal to the light transmitting portion 14 of the tubing 12. The light which passes through the light transmitting portion 14 of the tubing 12 and blood therein travels along the second path 22 to a second mirror 24 which is arranged in the second light path 22 on the other side of the tubing 12. This second mirror 24 is arranged to reflect light along a third path 26, which is 90° to the second path 22, thru an interference filter 27, which passes only light of the wavelength generated by the laser 16, to a photodetector 28 which is typically a silicon diode. The light sensed by the photodetector 28 is amplified by an amplifier circuit 30 and multiplied by a factor related to an approximated linear function such as represented by the slope of the line (linear curve) 32 shown in the graph of FIG. 2. The line 32 is explained below in connection with the description of FIG. 2.

Preferably, the laser 16 generates intense, coherent light within the red light spectrum. More specifically, the laser light has a wavelength within the range of 600–800 nanometers. In one preferred embodiment, the laser is a 0.5 milliwatt neonhelium laser which produces intense, coherent light at a wavelength of approximately 638.2 nanometers.

In empirical tests conducted with known concentrations of red blood cells in a blood solution, i.e., solutions having known hematocrits, intense, coherent laser light at 638.2 nanometers was passed through the blood solutions as they flowed through the tubing 12 and measurements of the transmitted light, i.e., of the optical density of the solution, were made. These measurements are as follows:

| Hematocrit | Absorbance |
| --- | --- |
| 70 | 0.83 |
| 68 | 0.80 |
| 67 | 0.75 |
| 61 | 0.70 |
| 60 | 0.61 |
| 55 | 0.48 |
| 51 | 0.40 |
| 48 | 0.28 |
| 44 | 0.18 |
| 39 | 0.02 |

Figure 2:
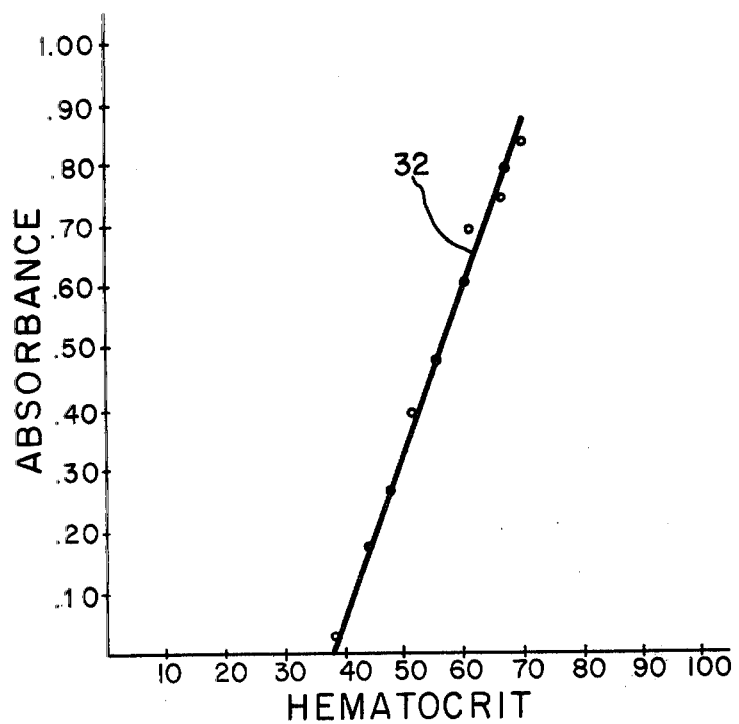
FIG. 2 is a graph of hematocrit versus light absorbance obtained from measurements of the amount of laser light transmitted through blood samples, each having a known hematocrit.

A plot of these measurements is illustrated in FIG. 2. Although the points plotted do not fall on a straight line, they are very close to the straight line 32 drawn through the plotted measurements. Alternatively, the line 32 can be developed mathematically with curve fitting procedures using regression analysis. The slope of such a straight line curve 32 (i.e., the linear function) can then be utilized for converting measurements of light transmitted through blood samples having an unknown hematocrit to obtain a rapid and fairly accurate measurement of hematocrit.

It will be appreciated that the passing of laser light through a blood sample and measuring optical density with the apparatus 10 is accomplished very quickly and the output signal can be quickly converted through suitable electronic circuitry into a digital display to give a rapid, relatively accurate indication of hematocrit. Also by using light in the red spectrum, where light absorption is not affected by differences in the oxygenation level of the hemoglobin in the red blood cells, measurements of optical density to obtain an indication of hematocrit are not affected by the oxygenation level of the hemoglobin.

Also, it will be appreciated that this technique for measuring hematocrit is non-invasive to the blood. In this respect, blood can be taken from a donor and passed directly, undiluted, through the tubing 12 and then returned to the donor through a sterile tubing 12 while at the same time a measurement of hematocrit is made without removing the blood from the sterile environment in the tubing 12 or invading such sterile environment in which the blood is situated.

The apparatus 10 of the present invention and the method for utilizing same to make a rapid, relatively accurate measurement of hematocrit of an unknown sample of blood is particularly useful in a blood separating apparatus and method of the type disclosed in U.S. application Ser. No. 843,222 now U.S. Pat. No. 4,185,629 filed Oct. 18, 1977 entitled: METHOD AND APPARATUS FOR PROCESSING BLOOD. In the method taught in that application and in the use of the apparatus disclosed in that application, whole blood being withdrawn from a donor and placed in a separation chamber in a centrifuge device for the separation of blood into its components is withdrawn at a volumetric rate related to the hematocrit of the blood of the donor. Also the volumetric rate of withdrawal of platelet-rich plasma withdrawn from the separation chamber were the whole blood is being centrifuged is withdrawn at a rate related to the hematocrit of the concentrated red blood cells being withdrawn from the same chamber. A rapid, relatively accurate determination of hematocrit of the blood in the whole blood being withdrawn from a donor and flowing into the apparatus and a rapid and relatively accurate determination of the hematocrit of the concentrated red blood cells withdrawn from the separation chamber in the apparatus can be obtained very quickly with the apparatus 10 of the present invention and utilized with suitable electronic circuitry to control the operation of the pumps providing the respective rates of volumetric flow of the whole blood and platelet-rich plasma.

More specifically, according to the teachings of U.S. application Ser. No. 843,222 it was found that efficient separation of blood should be obtained when the ratio of the rate of withdrawal of whole blood from a donor into the separation chamber to the rate of withdrawal of platelet-rich plasma from the separation chamber is caused to approach the following formula:

$$\frac{\text{Volumetric rate of blood in}}{\text{Volumetric rate of blood in} - \text{Volumetric rate of platelet rich plasma out}} = \frac{\text{Hematocrit of } RBC \text{ rich blood fluid out}}{\text{Hematocrit of blood in}}$$

The hematocrit of the blood in, with anticoagulant added, will be between 30 and 45 and the hematocrit of the RBC rich blood fluid out will be between 57 and 72. Accordingly two apparatus 10 of the present invention, each calibrated to measure hematocrit in those ranges, could be incorporated into the apparatus disclosed in the prior application together with suitable electronic and electrical control circuitry for operating the volumetric displacment pumps therein relative to the hematocrit sensed by the apparatus 10 as well as in accordance with a protocol disclosed in the prior application.

Also the method and apparatus 10 of the present invention can be utilized to make rapid, relatively accurate determinations of hematocrit can be made when examining a patient who appears to have symptomatology of a blood disorder or ailment. When used in this manner, the method and apparatus are utilized to make measurements of hematocrit within a range of 15 units of hematocrit, for example, between a hematocrit of 35 and a hematocrit of 50. Also, by limiting the range within which the apparatus 10 is used for measuring hematocrit, a more accurate measurement of hematocrit is made inasmuch as the function of hematocrit versus optical density (light transmission) between a hematocrit of 0 and a hematocrit of 100 is essentially non-linear, i.e., it is curvilinear. However, it approaches a linear function over relatively short spans of hematocrit such as a span of 15 or, as shown in FIG. 2, over a span of 30.

From the foregoing description it will be apparent that the method and apparatus for measuring hematocrit of the present invention have a number of advantages, some of which have been described above and others of which are inherent in the invention. Also, obvious modifications and variations can be made to the method and apparatus of the present invention without departing from the teachings of the invention. Accordingly, the scope of the invention is only to be limited as necessitated by the accompanying claims.

I claim:

1. Method for making a non-invasive, non-destructive, rapid, relatively accurate measurement in vivo of the hematocrit of undiluted blood including the steps of: passing the undiluted blood through a liquid confining means having a light transmitting portion; passing intense, coherent, monochromatic light through the light transmitting portion and undiluted blood; sensing the transmittance of light passed through the light transmitting portion and undiluted blood; producing an output signal related to the amount of transmitted light sensed and indicative of the light absorbed by the red blood cells; and multiplying the output signal by a proportionality factor determined from a curve function obtained from an approximated curve fit of absorbance v. hematocrit measurements for measurements of light absorbance by blood having known hematocrits to produce a corrected output signal which is indicative of the hematocrit of the undiluted blood and which can be used to control the flow rate of at least one pump pumping whole blood or a fluid component thereof in a blood processing apparatus.

2. The method according to claim 1 wherein said liquid confining means is a tubing.

3. The method according to claim 1 wherein the intense, coherent light is obtained from a laser light source.

4. The method according to claim 1 wherein the wavelength of light is within the red spectrum.

5. The method according to claim 1 wherein the light has a wavelength within the range of 600–800 nanometers.

6. The method according to claim 5 wherein the wavelength of the light is approximately 638.2 nanometers.

7. The method according to claim 1 wherein the hematocrit being measured is known to be within a range of 15 units of hematocrit.

8. The method according to claim 7 wherein the hematocrit being measured is known to be within 30 and 45.

9. The method according to claim 7 wherein the hematocrit being measured is known to be within 35 and 50.

10. The method according to claim 7 wherein the hematocrit is known to be within 57 and 72.

11. The method according to claim 1 wherein said curve function is a linear function and said approximated curve fit is a linear approximation.

12. An apparatus for making a non-invasive, non-destructive, rapid, relatively accurate measurement in vivo of the hematocrit of undiluted blood including: liquid confining means having a light transmitting portion and being adapted to receive undiluted blood therein; means for generating an intense, coherent, monochromatic light beam and for directing said light beam through said light transmitting portion of said liquid confining means and the undiluted blood; light sensing means arranged to detect the transmittance of light that passes through said light transmitting portion and through the undiluted blood from said light generating means and to produce an output signal related to the amount of transmitted light sensed and indicative of the light absorbed by the red blood cells; and means for multiplying the output signal generated by the transmitted light sensed by a proportionality factor determined from a curve function obtained from an approximated curve fit of absorbance v. hematocrit measurements for measurements of light absorbance by blood having known hematocrits thereby to produce a corrected output signal which is indicative of the hematocrit of the undiluted blood in said liquid confining means and which can be used to control the flow rate of at least one pump pumping whole blood or a fluid component thereof in a blood processing apparatus.

13. The apparatus according to claim 12 wherein said light generating means is operable to generate light having a wavelength falling within the red spectrum.

14. The apparatus according to claim 12 wherein said light generating means is operable to generate light having a wavelength within the range of 600–800 nanometers.

15. The apparatus according to claim 12 wherein said light generating means includes a laser light source.

16. The apparatus according to claim 15 wherein said laser light source is an 0.5 milliwatt, neon-helium laser which produces light at a wavelength of approximately 638.2. nanometers.

17. The apparatus according to claim 12 wherein said liquid confining means is a tubing having a light transmitting portion.

18. The apparatus according to claim 17 wherein said tubing is transparent.

19. The apparatus according to claim 12 wherein said light generating and directing means includes a laser light source arranged to direct a laser light beam along a first path, a mirror positioned in said first path for reflecting the laser light beam along a second path 90° from said first path and through said light transmitting portion of said liquid confining means, a second mirror arranged in said second path to receive transmitted light which has passed through said liquid confining means and to reflect that transmitted light along a third path 90° from said second path and to said light sensing means.

20. The apparatus according to claim 13 wherein said light sensing means comprises a photodetector including a silicon diode and an amplifier circuit.

21. The apparatus according to claim 12 wherein said curve function is a linear function and said approximated curve fit is a linear approximation.

22. The apparatus according to claim 12 wherein said light sensing means includes an interference filter which is positioned to receive transmitted light and which passes only light of the wavelength of light generated by said light generating means.

* * * * *